US012682986B2

(12) United States Patent
Hanaoka

(10) Patent No.: US 12,682,986 B2
(45) Date of Patent: Jul. 14, 2026

(54) PROPERTY PREDICTION SYSTEM, PROPERTY PREDICTION METHOD, AND PROPERTY PREDICTION PROGRAM

(71) Applicant: Resonac Corporation, Tokyo (JP)

(72) Inventor: Kyohei Hanaoka, Tokyo (JP)

( * ) Notice: Subject to any disclaimer, the term of this patent is extended or adjusted under 35 U.S.C. 154(b) by 399 days.

(21) Appl. No.: 18/556,092

(22) PCT Filed: Apr. 21, 2022

(86) PCT No.: PCT/JP2022/018416
§ 371 (c)(1),
(2) Date: Oct. 19, 2023

(87) PCT Pub. No.: WO2022/225009
PCT Pub. Date: Oct. 27, 2022

(65) Prior Publication Data
US 2024/0387005 A1 Nov. 21, 2024

(30) Foreign Application Priority Data
Apr. 23, 2021 (JP) ................................. 2021-073164

(51) Int. Cl.
*G16C 20/30* (2019.01)
*G16C 20/50* (2019.01)
*G16C 20/70* (2019.01)

(52) U.S. Cl.
CPC ............. *G16C 20/30* (2019.02); *G16C 20/50* (2019.02); *G16C 20/70* (2019.02)

(58) Field of Classification Search
CPC .......... G06N 20/10; G06N 3/045; G06N 3/09; G06N 5/01; G16C 20/30; G16C 20/50; G16C 20/70; G16C 60/00
See application file for complete search history.

(56) References Cited

U.S. PATENT DOCUMENTS

2002/0062307 A1* 5/2002 Gilbert .................. G16C 20/60

FOREIGN PATENT DOCUMENTS

| JP | 2019-028879 | | 2/2019 |
| JP | 2020085822 A | * | 6/2020 |
| WO | 2012/081723 | | 6/2012 |

OTHER PUBLICATIONS

Chiho Matsuda, "Reducing the Number of Experiments for New Material Development to 1/25 with AI Predictions", Nikkei XTECH [online], Japan, [accessed Nov. 26, 2024], Internet URL:https://xtech.nikkei.com/atcl/nxt/news/18/07572/, Apr. 15, 2020.

(Continued)

*Primary Examiner* — Yoshihisa Ishizuka
(74) *Attorney, Agent, or Firm* — SHIPWAY IP

(57) ABSTRACT

An input data generation system is an input data generation system generating input data for machine learning for predicting the properties of a material based on a raw material having a known structure, and includes at least one processor, in which at least one processor acquires partial structure data indicating a partial structure from a database, receives at least the input of raw material structure data for specifying the structure of the raw material and blending ratio data indicating a ratio of the blending of the raw material, generates partial structure input data indicating the partial structure existing in the structure of the raw material, on the basis of the partial structure data and the raw material structure data, generates input data by reflecting the blending ratio data on the partial structure input data of the raw material, and inputs the input data to a machine learning model.

7 Claims, 5 Drawing Sheets

(56)          References Cited

OTHER PUBLICATIONS

I. Oprisiu et al, "QSPR Approach to Predict Nonadditive Properties of Mixtures. Application to Bubble Point Temperatures of Binary Mixtures of Liquids", Molecular Informatics, vol. 31, No. 6-7, Hoboken, USA, Jul. 6, 2012, p. 491-p. 502.

Shibayama Shojiro et al, "Industrial Case Study: Identification of Important Substructures and Exploration of Monomers for the Rapid Design of Novel Network Polymers with Distributed Representation", Bulletin of the Chemical Society of Japan, vol. 94, No. 1, Jan. 15, 2021, p. 112-p. 121.

Cao Wei et al, "A novel method for predicting the flash points of binary mixtures from molecular structures", Safety Science, Elsevier, Amsterdam, NL, vol. 126, Mar. 3, 2020.

Christopher Kuenneth et al, "Copolymer Informatics with Multi-Task Deep Neural Networks", arxiv.org, Cornell University Library, 201 Olin Library Cornell University Ithaca, NY 14853, Mar. 25, 2021.

Extended Search Report in corresponding European Application No. 22791779.6, dated Mar. 3, 2025.

Okuno, Yoshishige, "Reducing the number of attempts to synthesize thermosetting polymers by AI analysis. https://www.admat.or.jp/ library/5975666db3de4b020a7803ae/5e90c92e8ab23b4546c25a2e. pdf", The 2019 project result report material of ultra-advanced materials ultra-high-speed development basic technology, Apr. 13, 2020, p. 1-p. 15.

Minami, Takuya, "Prediction of thermoset resin properties by using classification of raw materials and machine learning. https://www. jstage.jst.go.jp/article/ciqs/2018/0/2018_1PI0/_article/-char/ja", The Symposium on Chemoinformatics, Oct. 27, 2018, p. 1-p. 2.

Ikebata, Hisaki, "Polymer informatics utilizing PoLyInfo. https://www.jstage.jst.go.jp/article/cicsj/37/4/37_94/_article/-char/ja", CICSJBulletin, vol. 37, No. 4, Dec. 30, 2019, p. 94-p. 98.

Soei Patent and Law Firm, Statement of Related Matters, dated Jan. 10, 2024.

International Search Report dated Jul. 19, 2022 for PCT/JP2022/018415.

International Search Report dated Jul. 19, 2022 for PCT/JP2022/018416.

International Preliminary Report on Patentability with Written Opinion dated Nov. 2, 2023 for PCT/ JP2022/018415.

International Preliminary Report on Patentability with Written Opinion dated Nov. 2, 2023 for PCT/ JP2022/018416.

* cited by examiner

PROPERTY PREDICTION SYSTEM, PROPERTY PREDICTION METHOD, AND PROPERTY PREDICTION PROGRAM

CROSS-REFERENCE TO RELATED APPLICATIONS

This application is a 35 U.S.C. § 371 national phase application of PCT/JP2022/018416, filed on Apr. 21, 2022, which claims priority to Japanese Patent Application No. 2021-073164, filed on Apr. 23, 2021.

TECHNICAL FIELD

One aspect of the present disclosure relates to a property prediction system, a property prediction method, and a property prediction program.

BACKGROUND ART

In the related art, the structure of a molecule is acquired in a predetermined format, converted into vector information, and input to a machine learning algorithm to predict properties. For example, a method for predicting connectivity between a three-dimensional structure of a biological polymer and a three-dimensional structure of a compound by using machine learning is known (refer to Patent Literature 1 described below). In this method, a predicted three-dimensional structure of a composite body of the biological polymer and the compound is generated on the basis of the three-dimensional structure of the biological polymer and the three-dimensional structure of the compound, the predicted three-dimensional structure is converted into a predicted three-dimensional structure vector, and the predicted three-dimensional structure vector is determined by using a machine learning algorithm to predict the connectivity between the three-dimensional structure of the biological polymer and the three-dimensional structure of the compound.

CITATION LIST

Patent Literature

Patent Literature 1: Japanese Unexamined Patent Publication No. 2019-28879

SUMMARY OF INVENTION

Technical Problem

Recently, a technology of predicting the properties of a material by a neural network to which data indicating a structure, such as a molecular graph relevant to a material with a clear structure, is input has been known. However, in a case where there is little data to be input, it is difficult to predict the properties of the material by the machine learning based on the data. Therefore, there is a need for a mechanism for efficiently predicting the properties of a material based on the structure of a raw material.

Solution to Problem

A property prediction system of one aspect of the present disclosure is a property prediction system predicting the properties of a material based on a raw material having a known structure, and includes at least one processor, in which at least one processor is configured to acquire partial structure data indicating a partial structure from a database, receive at least the input of raw material structure data for specifying the structure of the raw material and blending ratio data indicating a ratio of the blending of the raw material, generate partial structure input data indicating the partial structure existing in the structure of the raw material, on the basis of the partial structure data and the raw material structure data, generate input data by reflecting the blending ratio data on partial structure input data of the raw material, and input the input data to a machine learning model.

Alternatively, a property prediction method of another aspect of the present disclosure is a property prediction method for predicting the properties of a material based on a raw material having a known structure, which is executed by a computer including at least one processor, and includes a step of acquiring partial structure data indicating a partial structure from a database, a step of receiving at least the input of raw material structure data for specifying the structure of the raw material and blending ratio data indicating a ratio of blending of the raw material, a step of generating partial structure input data indicating the partial structure existing in the structure of the raw material, on the basis of the partial structure data and the raw material structure data, a step of generating input data by reflecting the blending ratio data on partial structure input data of the raw material, and a step of inputting the input data to a machine learning model.

Alternatively, a property prediction program of another aspect of the present disclosure is a property prediction program for predicting the properties of a material based on a raw material having a known structure, and allows a computer to execute a step of acquiring partial structure data indicating a partial structure from a database, a step of receiving at least the input of raw material structure data for specifying the structure of the raw material and blending ratio data indicating a ratio of blending of the raw material, a step of generating partial structure input data indicating the partial structure existing in the structure of the raw material, on the basis of the partial structure data and the raw material structure data, a step of generating input data by reflecting the blending ratio data on partial structure input data of the raw material, and a step of inputting the input data to a machine learning model.

According to the aspects described above, partial structure input data expressing a known partial structure in the structure of the raw material is generated on the basis of the structure data of the raw material and the structure data of the partial structure acquired from the database, and the input data is generated by reflecting the blending ratio of the raw material on partial structure input data. Then, the generated input data is input to the machine learning model. As a result thereof, the input data narrowed down to the data of the partial structure set in advance from the entire structure of the raw material is generated, and by processing the input data with machine learning, it is possible to efficiently predict the properties of the material.

Advantageous Effects of Invention

According to the aspect of the present disclosure, it is possible to efficiently predict the properties of the material, on the basis of the structure of the raw material.

DESCRIPTION OF EMBODIMENTS

Figure 1:
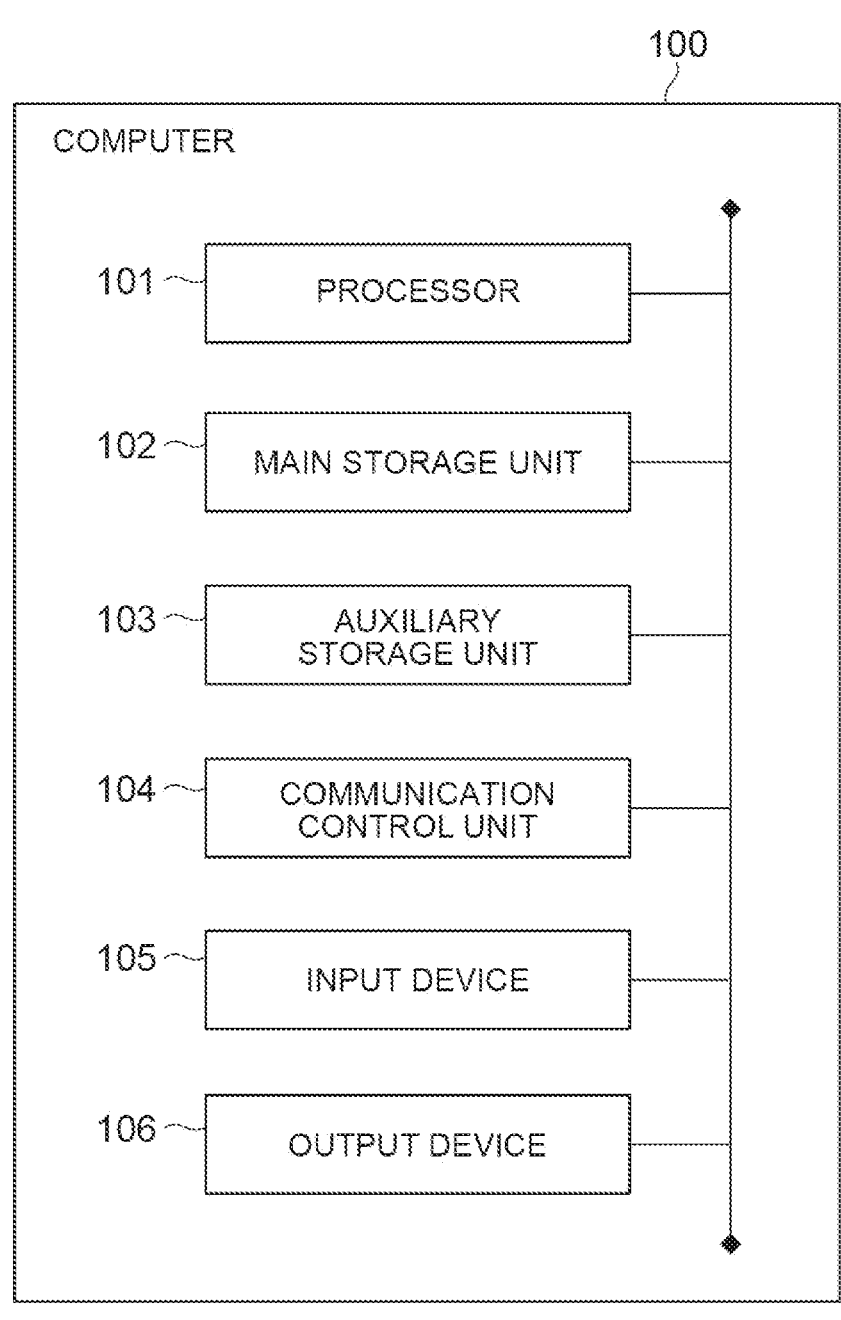
FIG. 1 is a diagram illustrating an example of a hardware configuration of a computer configuring a property prediction system according to an embodiment.

Hereinafter, an embodiment of the present invention will be described in detail, with reference to the attached drawings. Note that, in the description, the same reference numerals will be used in the same constituents or constituents with the same function, and the repeated description will be omitted.

[Outline of System]

A property prediction system 1 according to an embodiment is a computer system executing prediction processing of the properties of a multi-component substance, which is a material produced by blending a plurality of raw materials having a known structure at various ratios, by using a machine learning model. The raw material indicates a chemical substance having a clear molecular structure, which is used to generate the multi-component substance, and for example, is a monomer, a polymer, a low-molecular additive, and a monomolecule such as a solute molecule or a gas molecule. A plurality of types of molecules may be contained in one raw material. The multi-component substance is a chemical substance generated by blending a plurality of raw materials at a predetermined ratio, and for example, in a case where the raw material is a monomer or a polymer, the multi-component substance is a polymer alloy, in a case where the raw material is a solute molecule or a solvent, the multi-component substance is a mixed solution, and in a case where the raw material is a gas molecule, the multi-component substance is a mixed gas. However, a generation target of input data is not necessarily the multi-component substance, and may be a single-component substance generated from one raw material.

A prediction processing target of the property prediction system 1 is the properties of the multi-component substance. For example, in a case where the multi-component substance is a resin, the properties of the multi-component substance are a glass transition temperature, thermophysical properties such as a melting point, mechanical properties, bonding adhesiveness, and the like. In addition, in a case where the multi-component substance is another type of substance, the properties of the multi-component substance are the medicinal effect or the toxicity of a medical agent, riskiness such as the ignition point of a combustible material, appearance properties, suitability for a specific use, and the like. Machine learning is used in the prediction processing of the property prediction system 1. The machine learning is a method for autonomously finding out a law or a rule, on the basis of given information. A specific method of the machine learning is not limited. For example, the machine learning may be machine learning using a machine learning model, which is a computation model. More specifically, the computation model is a neural network. The neural network indicates an information processing model imitating the mechanism of the human cerebral nerve system. More specific examples of other computation models may include support vector regression (SVR), random forest, and the like, in addition to the neural network.

[Configuration of System]

The property prediction system 1 includes one or more computers. In the case of using a plurality of computers, such computers are connected via a communication network such as the internet or the intranet to logically construct one property prediction system 1.

FIG. 1 is a diagram illustrating an example of the general hardware configuration of a computer 100 configuring the property prediction system 1. For example, the computer 100 includes a processor (for example, a CPU) 101 executing an operating system, an application program, or the like, a main storage unit 102 including a ROM and a RAM, an auxiliary storage unit 103 including a hard disk, a flash memory, and the like, a communication control unit 104 including a network card or a wireless communication module, an input device 105 such as a keyboard, a mouse, and a touch panel, and an output device 106 such as a monitor and a touch panel display.

Each functional constituent of the property prediction system 1 is attained by reading a program set in advance on the processor 101 or the main storage unit 102 and allowing the processor 101 to execute the program. The processor 101 operates the communication control unit 104, the input device 105, or the output device 106 and reads and writes data in the main storage unit 102 or the auxiliary storage unit 103, in accordance with the program. Data or a database required for processing is stored in the main storage unit 102 or the auxiliary storage unit 103.

Figure 2:
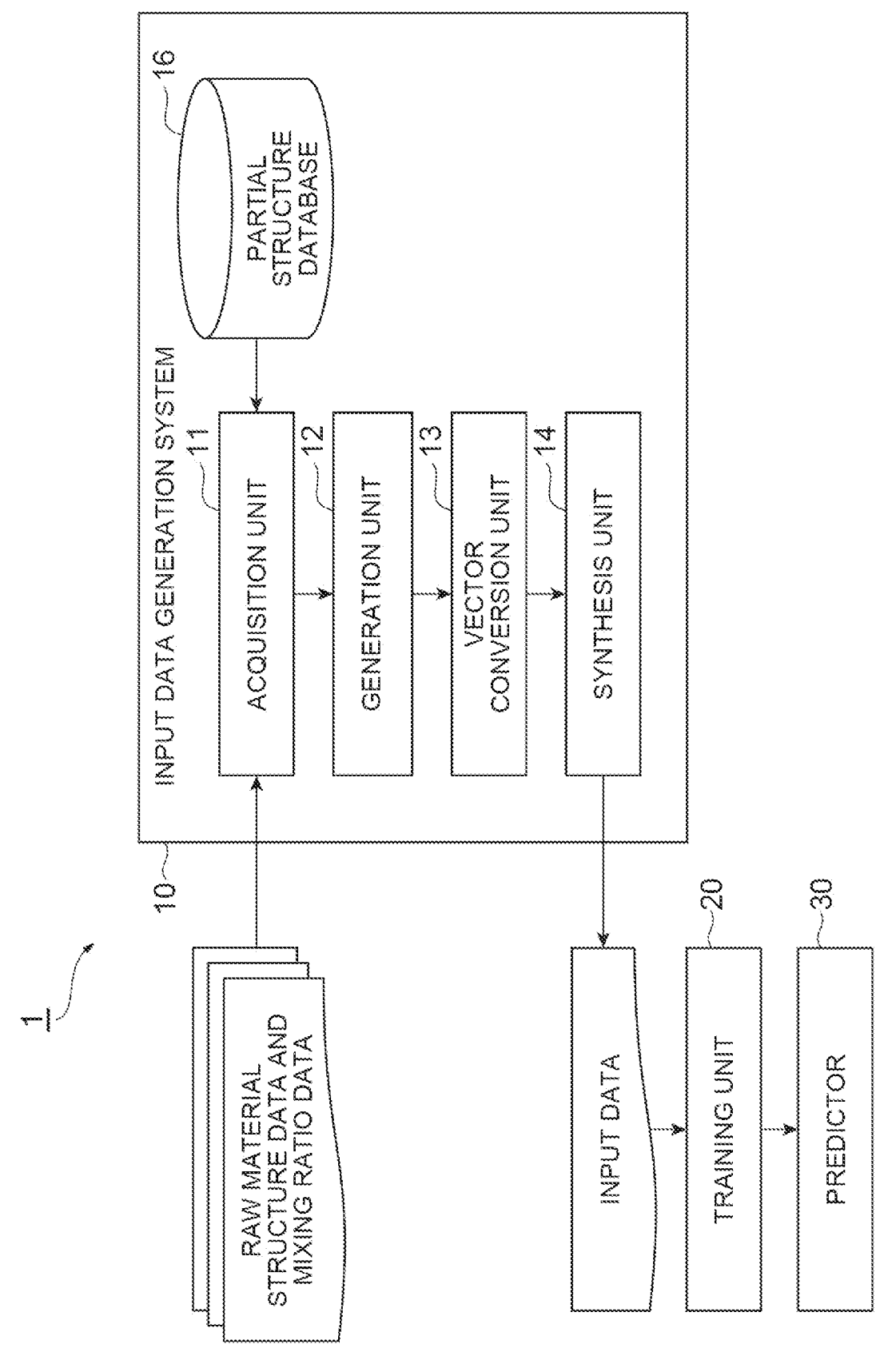
FIG. 2 is a diagram illustrating an example of a functional configuration of the property prediction system according to the embodiment.

FIG. 2 is a diagram illustrating an example of the functional configuration of the property prediction system 1. The property prediction system 1 includes an input data generation system 10, a training unit 20, and a predictor 30. The input data generation system 10, the training unit 20, and the predictor 30 may be constructed on the same computer 100, or a part thereof may be constructed on another computer 100. First, the functional configuration of the input data generation system 10 will be described. The input data generation system 10 includes an acquisition unit 11, a generation unit 12, a vector conversion unit 13, a synthesis unit 14, and a partial structure database 16, as a functional constituent.

The partial structure database 16 is a data storage means storing partial structure data indicating a combination of a plurality of partial structures in known molecules registered in advance in the input data generation system 10. As the partial structure data stored in the partial structure database 16, data (molecular structure information) indicating a known partial structure as a structure affecting the properties of a material is preferably used. Examples of such a partial structure include a structure represented by a molecular formula such as "OH", "CH$_3$", "CCC", or "NH". The partial structure data may be set in advance as data indicating a combination of a plurality of partial structures selected in accordance with the selection input of a user of the input data generation system 10 from the database in the input data generation system 10, or may be set in accordance with the selection of a user of an external computer or the like. The data (the molecular structure information) indicating the partial structure in the partial structure data may be a molecular graph, may be data indicating a molecular structure with a character such as a molecular formula, or may be data indicating a molecular structure with an image such as a structural formula. More specifically, such partial structure data may be data in a simplified molecular input line entry system (SMILES) notation, data in a MOL file format, or the like, in addition to the structural formula and the molecular graph.

However, the partial structure data is not necessarily set in accordance with the selection of the user. For example, for the properties of a prediction target of the property prediction system 1 (for example, the glass transition temperature of a polymer), a set of partial structures predicted to improve a prediction accuracy may be determined in advance by automatic verification processing, and the partial structure data may be set on the basis of the determined set of partial structures. In addition, the set of partial structures for improving the prediction accuracy may be automatically selected in the process of the machine learning, and the partial structure data may be set on the basis of the selected set of partial structures. In addition, regardless of the prediction of specific properties for a specific material, the set of partial structures for generally improving the prediction accuracy may be set in advance, and the partial structure data may be set on the basis of the set of partial structures.

The acquisition unit 11 is a functional constituent receiving the input of raw material structure data relevant to the structure of each molecule configuring the plurality of raw materials to be the basis of the multi-component substance, which is a prediction target, and blending ratio data indicating a ratio of the blending of each of the plurality of raw materials when it is assumed that the plurality of raw materials are blended to produce the multi-component substance. The acquisition unit 11 may acquire such data from the database in the input data generation system 10, in accordance with the selection input of the user of the input data generation system 10, or may acquire the data, in accordance with the selection of the user from the external computer or the like.

Specifically, the acquisition unit 11 acquires at least first raw material structure data for specifying the molecular structure of a first raw material, and second raw material structure data for specifying the molecular structure of a second raw material. Such raw material structure data is molecular structure information indicating a molecular structure. For example, such raw material structure data may be data for specifying the molecular structure with a number, an alphabetic character, a text, a vector, and the like, may be data for visualizing the molecular structure with two-dimensional coordinates, three-dimensional coordinates, and the like, or may be data of any combination of two or more data pieces described above. Each numerical value configuring the raw material structure data may be represented by a decimal system, or may be represented by other notation methods such as a binary system and a hexadecimal system. More specifically, such raw material structure data may be a structural formula, a molecular graph, data in a SMILES notation, data in a MOL file format, and the like. Here, the raw material data may not necessarily represent the entire molecules of the raw material, and may represent a partial structure in the molecules of the raw material.

Figure 3A:
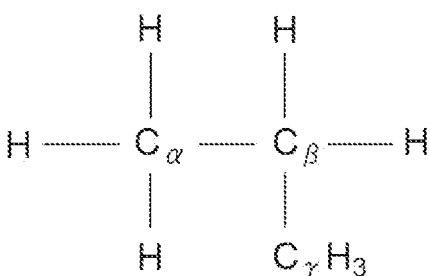
FIGS. 3A and 3B are diagrams illustrating an example of a molecular structure specified with raw material structure data acquired by an acquisition unit 11 in FIG. 2.
Figure 3B:
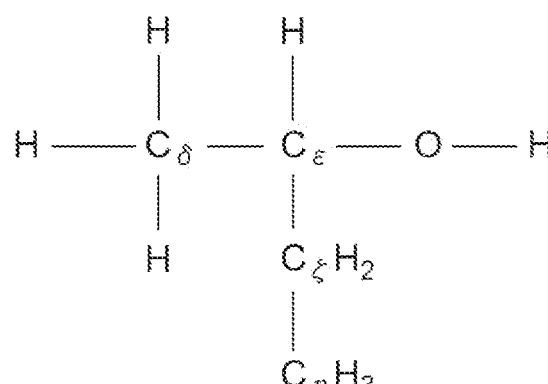

FIGS. 3A and 3B illustrate an example of a molecular structure specified by the raw material structure data, in which FIG. 3A illustrates an example of a molecular structure specified by the first raw material structure data, and FIG. 3B illustrates an example of a molecular structure specified by the second raw material structure data. The first raw material structure data is data capable of specifying the molecular structure of the first raw material. Similarly, the second partial structure data is data capable of specifying the molecular structure of the second raw material.

In addition, as the blending ratio data indicating a ratio r of the plurality of raw materials, the acquisition unit 11 may acquire data indicating a ratio itself of each of the raw materials, may acquire data indicating a blending ratio between the plurality of raw materials, or may acquire data indicating the blending amount (the weight, the volume, and the like) of each of the plurality of raw materials in an absolute value or a relative value. For example, the acquisition unit 11 acquires Ratio $r_1$="0.5" of a first monomer, which is the first raw material, and Ratio $r_2$="0.5" of a second monomer, which is the second raw material. Further, the acquisition unit 11 acquires the partial structure data indicating the combination of the plurality of partial structures in the registered known molecules from the partial structure database 16.

The generation unit 12 searches for the partial structure indicated by the partial structure data in the molecular structure of the raw material, on the basis of a plurality of raw material structure data pieces and partial structure data pieces acquired by the acquisition unit 11, and specifies the number of the partial structure existing in the molecular structure. For example, in a case where the partial structure indicated by the partial structure data includes a partial structure such as "OH", "$CH_3$", "CCC", and "NH", the generation unit 12 specifies the existence of the partial structure "$CH_3$" and the partial structure "CCC", together with the respective numbers "2" and "1", from the molecular structure indicated by the first raw material structure data illustrated in FIG. 3A. Similarly, the generation unit 12 specifies the existence of the partial structures "OH", "$CH_3$", and "CCC", together with the respective numbers "1", "2", and "2", from the molecular structure indicated by the second raw material structure data illustrated in FIG. 3B. Note that, the number of partial structures acquired here may be data indicating a number normalized such that the total number of partial structures in the molecules of the same raw material is "1".

In addition, the generation unit 12 generates partial structure input data D0 for each of the partial structures included in the molecules of the plurality of raw materials, on the basis of the searched partial structure. Specifically, the partial structure input data D0 in which molecular structure information relevant to the partial structure included in the raw material, the data of the ratio r relevant to the raw material, and number data relevant to the partial structure are combined is generated for each of the plurality of raw materials, on the basis of the molecular structure information corresponding to the partial structure searched by the acquisition unit 11. Then, the generation unit 12 repeats the generation of the partial structure input data D0 for all the partial structures searched for each of the plurality of raw materials.

The vector conversion unit 13 converts each of all the partial structure input data pieces D0 generated by the generation unit 12 into one vector data piece. For example, the vector conversion unit 13 performs the conversion to a vector $V_M$ by molecular description, with reference to the molecular structure information relevant to each of the partial structures included in the partial structure input data D0. According to the molecular description, molecular characteristics indicated by the molecular structure information can be represented as a numerical string, on the basis of the chemical structure thereof. Any method can be adopted as a molecular description method insofar as the molecular structure is vectorized by the method, and for example, Extended Connectivity FingerPrints (ECFP), MACCS FingerPrints, PubChem FingerPrints, Substructure FingerPrints, Estate FingerPrints, BCI FingerPrints, Molprint2D FingerPrints, Pass base FingerPrints, and the like can be adopted. Further, the vector conversion unit 13 generates partial structure input data D by combining the data of the ratio r relevant to the raw material having a partial structure, and the number data of the partial structure in the raw material, with the vector $V_M$ generated for each of the partial structures.

The synthesis unit 14 compiles the vector $V_M$ for each of all the partial structures for each of the plurality of raw materials, which is converted by the vector conversion unit 13, on one vector data piece to generate synthetic input data F. For example, in a case where there are two partial structure input data pieces $D_{1,1}$ and $D_{1,2}$ corresponding to the partial structures "CH$_3$" and "CCC" of the first raw material, and three partial structure input data pieces $D_{2,1}$, $D_{2,2}$, and $D_{2,3}$ corresponding to the partial structures "OH", "CH$_3$", and "CCC" of the second raw material, the synthesis unit 14 generates the synthetic input data F in which five vectors $V_M$ corresponding to such five partial structure input data pieces $D_{1,1}$, $D_{1,2}$, $D_{2,1}$, $D_{2,2}$, and $D_{2,3}$ are compiled.

In this case, the synthesis unit 14 reflects the blending ratio data and the number data corresponding to each of the partial structures on five vectors $V_M$ corresponding to such five partial structure input data pieces $D_{1,1}$, $D_{1,2}$, $D_{2,1}$, $D_{2,2}$, and $D_{2,3}$ to obtain the weighted average of five vectors $V_M$ and generate the synthetic input data F. More specifically, the synthesis unit 14 multiplies the element of each of five vectors $V_M$ corresponding to the partial structure input data pieces $D_{1,1}$, $D_{1,2}$, $D_{2,1}$, $D_{2,2}$, and $D_{2,3}$, by the ratio r and the number n corresponding to each of the partial structures, and then, adds (or averages) the element of each of five vectors $V_M$ to generate the synthetic input data F. For example, the synthesis unit 14 multiplies the vector $V_M$ corresponding to the partial structure of the first raw material by a value obtained by multiplying the ratio $r_1$ of the first raw material and the number n of the partial structure together, and multiplies the vector $V_M$ corresponding to the partial structure of the second raw material by a value obtained by multiplying the ratio $r_2$ of the second raw material and the number n of the partial structure together. As an example, the vector $V_M$ corresponding to the partial structure "CH$_3$" of the first raw material illustrated in FIG. 3A is multiplied by a value ($0.5 \times 2 = 1.0$) obtained by multiplying Ratio $r_1 = 0.5$ and "2", which is the number of the partial structure, together, and the vector $V_M$ corresponding to the partial structure "OH" of the second raw material illustrated in FIG. 3B is multiplied by a value ($0.5 \times 1 = 0.5$) obtained by multiplying Ratio $r_2 = 0.5$ and "1", which is the number of the partial structure, together. Here, the reflection of the ratio and the number data may be performed by adding the value obtained by multiplying the ratio r and the number n together to each of the elements of the vector $V_M$, or may be performed by concatenating the value obtained by multiplying the ratio r and the number n together to the element of the vector. In addition, more generally, the synthesis unit 14 may generate a vector by using a function of outputting a single vector in accordance with a certain rule, with the vector, the blending ratio, and the number relevant to all the partial structures as input, or may generate a single vector in one processing without dividing the processing into a step of reflecting the blending ratio and a step of adding the vector.

Further, the synthesis unit 14 outputs the generated synthetic input data F to the outside such that the data is input to an external machine learning model. That is, the output synthetic input data F is read by the training unit 20 in a computer connected to the outside of the input data generation system 10. Then, in the training unit 20, a learned model is generated by inputting the synthetic input data F to the machine learning model as an explanatory variable, together with any training label. Further, a machine learning model in the predictor 30 is set on the basis of the learned model generated by the training unit 20. Here, the training unit 20 and the predictor 30 may be the same functional unit. Then, by inputting the synthetic input data F generated by the input data generation system 10 to the machine learning model in the predictor 30, the predictor 30 generates and outputs a prediction result of the properties of the multi-component substance. Note that, the training unit 20 and the predictor 30 may be configured in the same computer as the computer 100 configuring the input data generation system 10, or may be configured in a computer different from the computer 100.

In an example, the training unit 20 generates a learned model using a neural network. The learned model is generated by a computer processing training data including a plurality of combinations of input data and output data. The computer calculates the output data by inputting the input data to the machine learning model, and obtains an error between the calculated output data and the output data indicated by the training data (that is, an error between an estimation result and a ground truth). Then, the computer updates given parameters of the neural network, which is the machine learning model, on the basis of the error. The computer generates the learned model by repeating such learning. The processing of generating the learned model can be referred to as a learning phase, and the processing of the predictor 30 using the learned model can be referred to as an operation phase.

[Operation of System]

Figure 4:
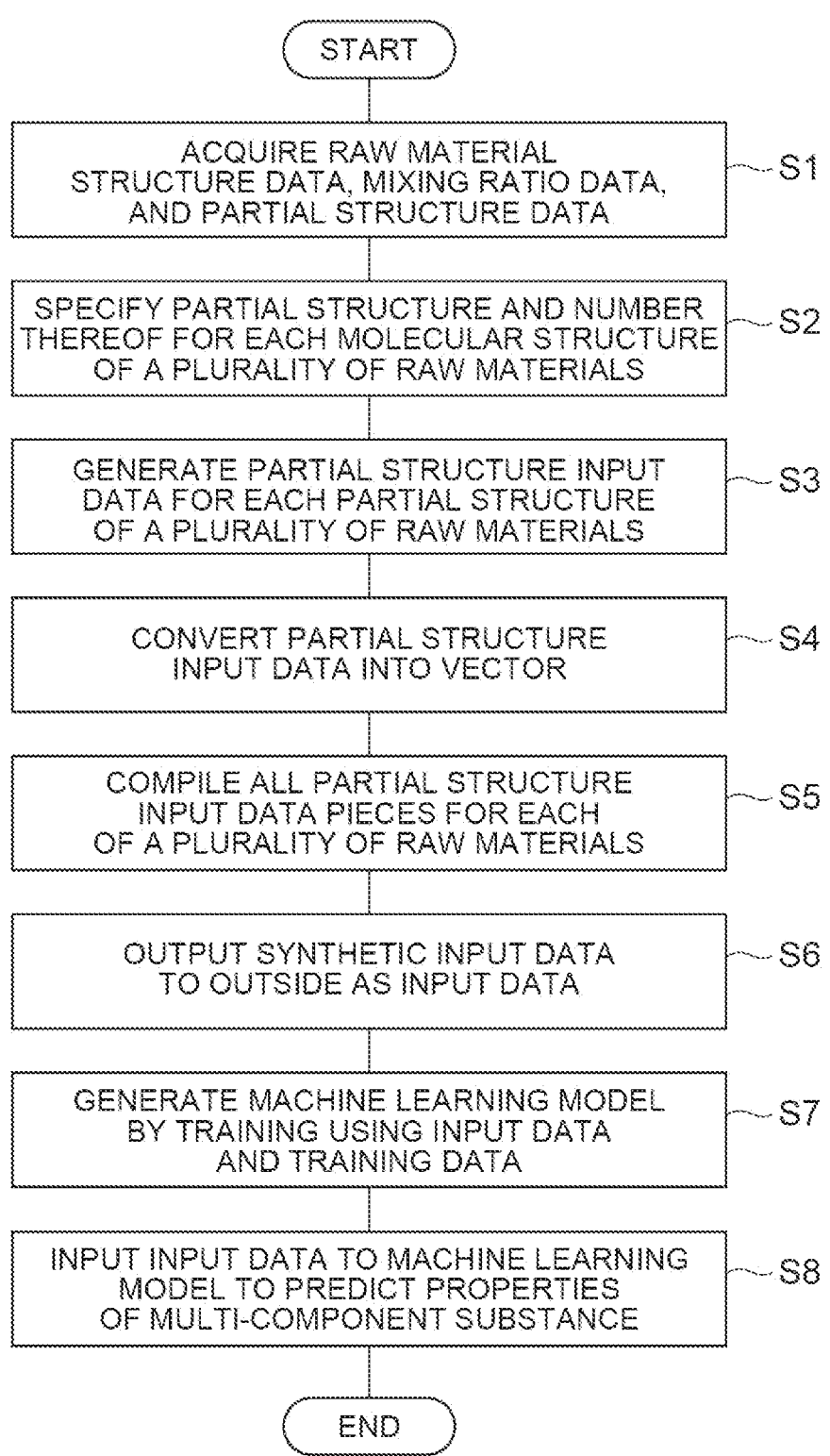
FIG. 4 is a flowchart illustrating an example of an operation of the property prediction system according to the embodiment.

The operation of the property prediction system 1 will be described, and a property prediction method according to this embodiment will be described, with reference to FIG. 4. FIG. 4 is a flowchart illustrating an example of the operation of the property prediction system 1.

First, in a case where input data generation processing is started in accordance with the instruction input of the user of the input data generation system 10, the acquisition unit 11 is allowed to acquire the raw material structure data and the blending ratio data for each of the plurality of raw materials, and acquire the partial structure data indicating the plurality of known partial structures from the partial structure database 16 (step S1). Next, the generation unit 12 is allowed to search for the partial structure in the molecular structure of the raw material indicated by each of the raw material structure data pieces to specify the partial structure in the molecular structure and the number thereof (step S2). Further, the generation unit 12 is allowed to generate the partial structure input data D0 for each of the partial structures in the molecular structures of the plurality of raw materials (step S3). After that, the vector conversion unit 13 is allowed to convert each of all the partial structure input data pieces D0 into one vector $V_M$ in a vector format, and combine the data of the ratio r relevant to the raw material having the partial structure, and the number data of the partial structure in the raw material, with the vector $V_M$, to generate the partial structure input data D (step S4).

Next, the synthesis unit 14 is allowed to compile the vectors $V_M$ corresponding to all the partial structure input data pieces D for each of the plurality of raw materials to generate the synthetic input data F (step S5). In this case, the synthesis unit 14 is allowed to compute the weighted average of the vectors $V_M$ while reflecting the blending ratio data and the number data on each of the vectors $V_M$ to generate the synthetic input data F. After that, the synthesis unit 14 is allowed to output the synthetic input data F to the training unit 20 as input data for machine learning (step S6). In this case, the reflection of the ratio and the number on the vector $V_M$ is performed by multiplying, adding, or concatenating the value obtained by multiplying the ratio and the number together with respect to each of the vectors $V_M$. In addition, more generally, the synthesis unit 14 may generate the vector by using the function of outputting the single vector in accordance with a certain rule, with the vector, the blending ratio, and the number relevant to all the partial structures as input, or may generate the single vector in one processing without dividing the processing into the step of reflecting the blending ratio and the step of adding the vector.

Next, in the training unit 20, the learning phase is executed, and the learned model is generated by learning using the input data and the training data (step S7). Then, the generated learned model is set in the predictor 30, and the predictor 30 is allowed to execute the operation phase by using the input data newly acquired from the input data generation system 10, and generate and output the prediction result of the properties of the multi-component substance (step S8).

[Program]

A property prediction program for allowing a computer or a computer system to function as the property prediction system 1 includes a program code for allowing the computer system to function as the acquisition unit 11, the generation unit 12, the vector conversion unit 13, the synthesis unit 14, the partial structure database 16, the training unit 20, and the predictor 30. Such a property prediction program may be provided by being regularly recorded in a physical recording medium such as a CD-ROM, a DVD-ROM, and a semiconductor memory. Alternatively, the property prediction program may be provided via a communication network as a data signal superimposed on a carrier wave. The provided property prediction program, for example, is stored in the auxiliary storage unit 103. By the processor 101 reading and executing the property prediction program from the auxiliary storage unit 103, each of the functional constituents described above is attained.

[Effect]

As described above, according to the embodiment described above, the partial structure input data D expressing the known partial structure in the structure of the raw material is generated on the basis of the structure data of the raw material and the structure data of the partial structure acquired from the database, and the input data is generated by reflecting the ratio of the raw material on the partial structure input data D, and compiling the partial structure input data D. Then, the generated input data is input to the machine learning model. As a result thereof, the input data narrowed down to the data of the partial structure data in advance from the entire structure of the raw material is generated, and by processing the input data with the machine learning, it is possible to efficiently predict the properties of the material.

In addition, in the embodiment described above, the input of the raw material structure data relevant to the plurality of raw materials, and the blending ratio data indicating the ratio of the blending of each of the plurality of raw materials is received, the partial structure input data is generated for each of the plurality of raw materials, and the input data is generated by reflecting the blending ratio data relevant to the plurality of raw materials on the partial structure input data of the plurality of raw materials. In this case, the partial structure input data D0 expressing the known partial structure is generated on the basis of the raw material structure data for each of the plurality of raw materials, and the synthetic input data F is generated by reflecting the ratio of each of the plurality of raw materials on the partial structure input data D0 for each of the plurality of raw materials. Then, the generated synthetic input data F is input to the machine learning model. As a result thereof, by processing the input data with the machine learning for the multi-component substance to be produced on the basis of the plurality of raw materials, it is possible to efficiently predict the properties of the substance.

In addition, in the embodiment described above, the number of the partial structure existing in the structure of the raw material is specified, and the input data is generated by reflecting the value obtained by multiplying the blending ratio data and the number of the partial structure together on the partial structure input data of the raw material. In this case, the number of partial structures in the molecules of the raw material is specified, and the ratio of the raw material and the number of partial structures can be reflected on the partial structure input data D0. As a result thereof, it is possible to accurately predict the properties of the multi-component substance based on the raw material.

Further, in the embodiment described above, the input data to be input to the machine learning model is generated by multiplying, adding, or concatenating a value based on the blending ratio data with respect to the vector included in the partial structure input data D, and compiling the multiplied, added, or concatenated vector on one vector. Accordingly, it is possible to effectively and simply reflect the ratio of the raw material on the partial structure input data D relevant to the partial structure of the raw material. As a result thereof, the prediction accuracy of the properties of the multi-component substance is improved.

Modification Example

The present invention has been described in detail, on the basis of the embodiment. However, the present invention is not limited to the embodiment described above. The present invention can be variously modified within a range not departing from the gist thereof.

In the embodiment described above, an example has been described in which the input data generation system 10 generates the synthetic input data F by combining the partial structure input data D0 of two raw materials, but the partial structure input data D0 of three or more raw materials may be combined together with the ratio thereof, or only the partial structure input data D of one raw material may be generated as the input data and used in the property prediction of the single-component substance.

In addition, a certain conversion rule provided in the vector conversion unit 13 of the input data generation system 10 may be other rules.

Figure 5:
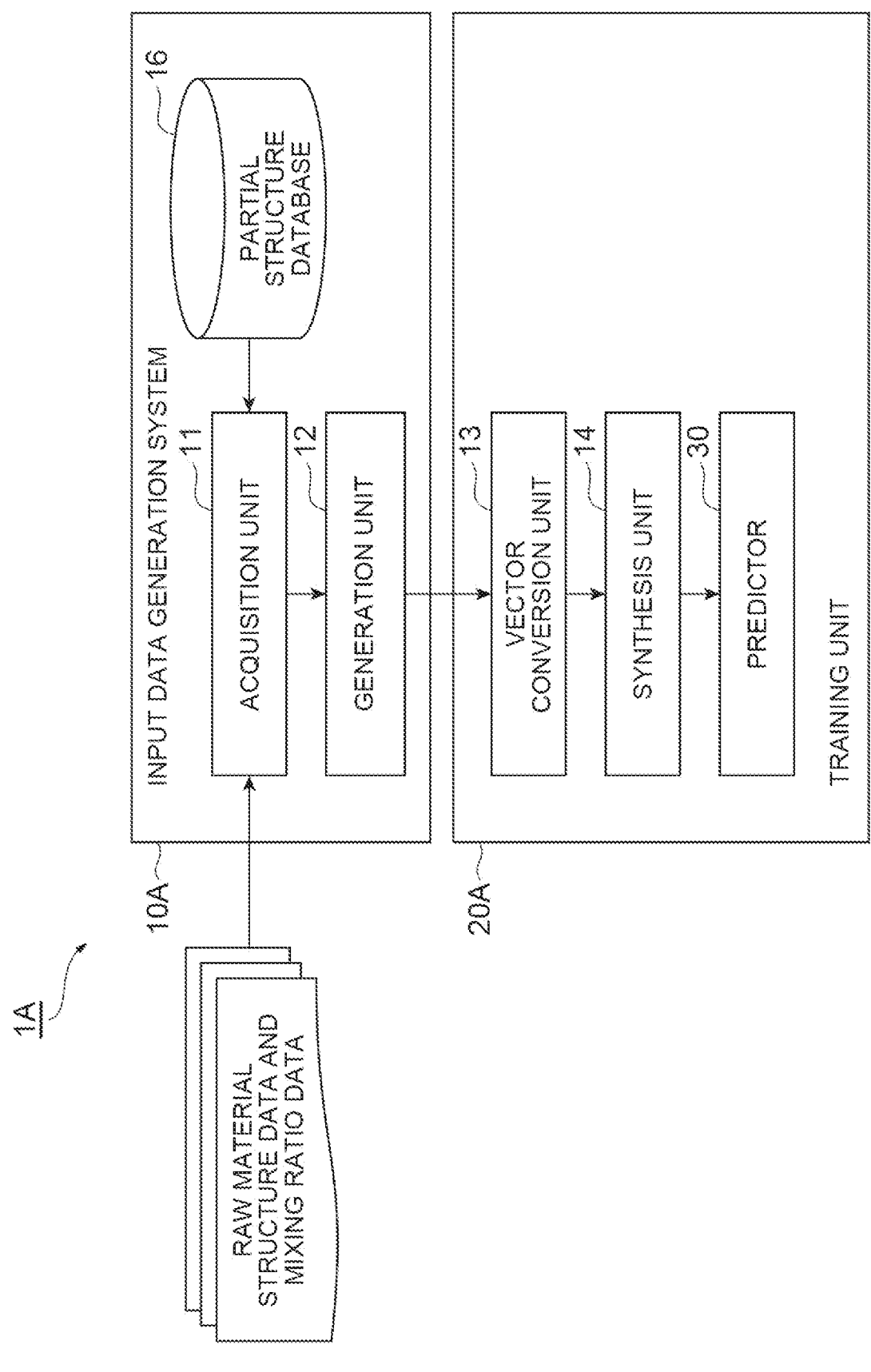
FIG. 5 is a diagram illustrating an example of a functional configuration of a property prediction system according to a Modification Example.

FIG. 5 illustrates the configuration of a property prediction system 1A according to a Modification Example. In this Modification Example, the functions of the vector conversion unit 13, the synthesis unit 14, and the predictor 30 are provided in a training unit 20A. Then, in the training unit 20A, a vectorization function, a data synthesizing function, and a reflection function using blending ratio data and number data of such functional units are attained by using a machine learning model of a neural network integrated with the predictor 30. In this case, the training unit 20A inputs the partial structure input data D0 for each of the partial structures generated by the generation unit 12 of an input data generation system 10A to the machine learning model.

Here, the training unit 20A inputs the partial structure input data D0 to the machine learning model using the neural network. The partial structure information included in the input partial structure input data D0 is a structural formula, a molecular graph, data in a SMILES notation, data in three-dimensional coordinates, and the like. Hereinafter, an example will be described in which a molecular graph is input to the machine learning model as the partial structure input data D0.

That is, in the Modification Example described above, the generation unit 12 generates a node vector set FV corresponding to a node set V in Molecular Graph G=(V,E) in a one-to-one manner, and an edge vector set FE corresponding to an edge set E in the molecular graph in a one-to-one manner, with reference to molecular graph data, which is the molecular structure information for each of the searched partial structures. The node vector is a vector for specifying atoms of a node, and for example, is a vector element in which numerical values (an atomic number, an electronegativity, and the like) indicating the characteristics of the atoms configuring the node that is each member of the set are sequentially arranged. The edge vector is a vector for specifying the properties of a bond between the nodes, and for example, is a vector element in which numerical values (a bond order, a bond distance, and the like) indicating the characteristics of an edge that is each member of the set are sequentially arranged. Further, the generation unit 12 generates the partial structure input data D0 by combining the original molecular graph data of a partial structure, the data of the ratio r relevant to the raw material having the partial structure described above, and the number data of the partial structure described above in the raw material with the node vector set FV and the edge vector set FE. Then, the generation unit 12 repeats the generation of the partial structure input data D0 for all the partial structures searched for each of the plurality of raw materials. In addition, the generation unit 12 may combine only the data of the ratio r and the number data with the molecular structure information, which is the molecular graph, to generate the partial structure input data D0.

The training unit 20A receives all the partial structure input data pieces D0 for each of the plurality of raw materials, and generates the synthetic input data F, which is one vector, on the basis of the partial structure input data D0, by the vector conversion unit 13 and the synthesis unit 14 attained by the machine learning model using the neural network. Then, the synthetic input data F is input to the predictor 30 in the same machine learning model. Note that, in this Modification Example, the function of the predictor 30 may be separated from the machine learning model of the training unit 20A and attained by another machine learning model.

In addition, the input data generation system 10 of the embodiment described above may have a function of merging and expressing the molecular structure information, the blending ratio data, and the number data for each of the partial structures in one molecular graph. In this case, as with the generation unit 12 of the property prediction system 1A according to the Modification Example described above, the partial structure input data D0 is generated. Then, the blending ratio data and the number data are reflected on the molecular graph included in the partial structure input data D0 for each of the partial structures. Specifically, the blending ratio data and the number data are reflected on a feature vector included in the node vector set FV and the edge vector set FE included in the partial structure input data D0. Further, the synthetic input data F is generated by merging the molecular graph included in the partial structure input data D0 for each of the partial structures on which the blending ratio is reflected in one molecular graph data piece. In such a case, the input data generation system 10 attains the property prediction by inputting the generated molecular graph for each of the multi-component materials to the machine learning model capable of generating prediction data by the input of the molecular graph.

In addition, when converting the partial structure input data D for each of the plurality of raw materials into a one-dimensional vector, the vector conversion unit 13 of the input data generation system 10 of the embodiment described above may reflect a value indicating a difference in the raw materials on the vector. For example, the vector conversion unit 13 may concatenate a vector indicating a difference in the raw materials with a one-hot vector to the vector $V_M$. In addition, the vector conversion unit 13 may concatenate a vector indicating a difference in the raw materials with dispersion expression to the vector $V_M$. Accordingly, even in a case where the partial structures are the same, it is possible to reflect a difference in the raw materials on the partial structure input data D for each of the raw materials. As a result thereof, the prediction accuracy of the properties of the multi-component substance is further improved. In addition, the synthesis unit 14 may concatenate a vector in which the blending amounts of a raw material group having an unknown molecular structure are arranged to the synthetic input data F. Accordingly, even in the case of including the raw material having an unknown molecular structure, it is possible to predict the properties.

On the other hand, in the case of using a neural network with the graph as described in the Modification Example described above as input, and the vector indicating a difference in the raw materials is added, the input data generation system 10 of the embodiment described above may concatenate the vector to the node vector of each of the raw materials generated by the generation unit 12. Note that, the vector conversion unit 13 of the property prediction system 1A according to the Modification Example described above may be attained by the machine learning model of the neural network. In this case, the vector conversion unit 13 may be operated to reflect the vector indicating a difference in the raw materials on the vector of an intermediate layer of the neural network.

In addition, the synthesis unit 14 may select and synthesize the data of some partial structures from all the partial structures for each of the plurality of raw materials searched by the generation unit 12, in accordance with a predetermined rule, to generate the synthetic input data F. For example, as the predetermined rule, it is considered to select a part from the data of the partial structures similar to each other.

In addition, in the embodiment described above, a plurality of types of partial structure data pieces may be set in advance in the partial structure database. For example, it is considered to set a plurality of types of partial structure data pieces in which one structure is sequentially deleted from the plurality of partial structures. In this case, the input data generation system 10 has a function of building an ensemble learning machine by acquiring the plurality of types of partial structure data pieces from the partial structure database 16, generating a plurality of types of input data pieces using the plurality of types of partial structure data pieces, and inputting the plurality of types of input data pieces to a plurality of machine learning models. Accordingly, it is possible to input the input data based on search results of various partial structures to a plurality of learning machines, attain ensemble learning for averaging the prediction results of the plurality of learning machines, and performing regression or classification with the majority decision, and further improve the prediction accuracy of the properties of the multi-component substance.

In addition, in the embodiment described above, as the synthetic input data F, a feature vector based on data indicating the entire structure of the molecules of the raw material may be used together. For example, such a feature vector may be used in the property prediction by being concatenated to the synthetic input data F, or input data based on such a feature vector may be used in the ensemble learning.

A processing procedure of an input data generation method executed by at least one processor is not limited to an example in the embodiment described above. For example, a part of the steps (the processing) described above may be omitted, or each of the steps may be executed in another order. In addition, any two or more steps among the steps described above may be combined, or a part of the steps may be corrected or deleted. Alternatively, other steps may be executed in addition to each of the steps described above. For example, the processing of steps S8 and S9 may be omitted.

In the present disclosure, an expression "at least one processor executes first processing, executes second processing, . . . , and executes n-th processing.", or an expression corresponding thereto indicates a concept including a case where an executor (that is, the processor) of n processing pieces of the first processing to the n-th processing is changed in the middle. That is, the expression indicates a concept including both of a case where all of n processing pieces are executed by the same processor and a case where the processor is changed in n processing pieces, in accordance with any policy.

REFERENCE SIGNS LIST 1, 1A: property prediction system, 10, 10A: input data generation system, 100: computer, 101: processor, 11: acquisition unit, 12: generation unit, 13: vector conversion unit, 14: synthesis unit, 16: partial structure database, 20: training unit, 30: predictor.

The invention claimed is:

1. A property prediction system predicting properties of a material based on a plurality of raw materials having a known structure, the system comprising at least one processor, wherein the at least one processor is configured to:

acquire partial structure data indicating a partial structure from a database;

receive input comprising:

raw material structure data for specifying the structure of each of the raw materials; and blending ratio data indicating a ratio of blending of each of the raw materials;

generate partial structure input data indicating the partial structure existing in the structure of each of the raw materials, on the basis of the partial structure data and the raw material structure data of each of the raw materials, by converting the partial structure data to a vector using molecular description, wherein the vector corresponds to the partial structure input data of each of the raw materials;

generate input data by:

multiplying each of elements of the vector by the blending ratio data corresponding to the partial structure input data, and adding or averaging elements of each of the vectors for each of the raw materials;

input the input data to a machine learning model; and cause the machine learning model to output predicting result of properties of the material.

2. The property prediction system according to claim 1, wherein the at least one processor is configured to:

specify a number of the partial structure existing in the structure of the raw material; and generate the input data by reflecting a value obtained by multiplying the blending ratio data and the number of the partial structure together on the partial structure input data of the raw material.

3. The property prediction system according to claim 1, wherein the partial structure input data is molecular structure information indicating a structure of the partial structure.

4. The property prediction system according to claim 1, wherein the at least one processor generates the input data by further reflecting a value indicating a difference in the raw materials on a plurality of data pieces, which are partial structure input data for each of the plurality of raw materials, and compiling the data pieces on one data piece.

5. The property prediction system according to claim 1, wherein the at least one processor acquires a plurality of types of the partial structure data pieces from the database;

generates a plurality of types of the input data pieces by using the plurality of types of partial structure data pieces; and inputs the plurality of types of input data pieces to a plurality of machine learning models to build an ensemble learning machine.

6. A property prediction method for predicting properties of a material based on a plurality of raw materials having a known structure, the method being executed by a computer including at least one processor, the method comprising:

acquiring partial structure data indicating a partial structure from a database;

receiving input comprising:

raw material structure data for specifying the structure of each of the raw materials; and blending ratio data indicating a ratio of blending of each of the raw materials;

generating partial structure input data indicating the partial structure existing in the structure of each of the raw materials, on the basis of the partial structure data and the raw material structure data of each of the raw materials, by converting the partial structure data to a vector using molecular description, wherein the vector corresponds to the partial structure input data of each of the raw materials;

generating input data by:

multiplying each of elements of the vector by the blending ratio data corresponding to the partial structure input data, and adding or averaging elements of each of the vectors for each of the raw materials;

inputting the input data to a machine learning model; and causing the machine learning model to output predicting result of properties of the material.

7. A non-transitory computer-readable storage medium storing a property prediction program for predicting properties of a material based on a plurality of raw materials having a known structure, the program allowing a computer to execute:

acquiring partial structure data indicating a partial structure from a database;

receiving input comprising:

raw material structure data for specifying the structure of each of the raw materials; and blending ratio data indicating a ratio of blending of each of the raw materials;

generating partial structure input data indicating the partial structure existing in the structure of each of the raw materials, on the basis of the partial structure data and the raw material structure data of each of the raw materials, by converting the partial structure data to a vector using molecular description, wherein the vector corresponds to the partial structure input data of each of the raw materials;

generating input data by:

multiplying each of elements of the vector by the blending ratio data corresponding to the partial structure input data, and adding or averaging elements of each of the vectors for each of the raw materials;

inputting the input data to a machine learning model; and causing the machine learning model to output predicting result of properties of the material.

* * * * *